United States Patent [19] [11] 4,226,938
Yoshida et al. [45] * Oct. 7, 1980

[54] METHOD FOR IMMOBILIZING ENZYMES

[75] Inventors: Masaru Yoshida; Minoru Kumakura; Isao Kaetsu, all of Takasaki, Japan

[73] Assignee: Japan Atomic Energy Research Institute, Tokyo, Japan

[*] Notice: The portion of the term of this patent subsequent to Dec. 4, 1996, has been disclaimed.

[21] Appl. No.: 944,444

[22] Filed: Sep. 21, 1978

Related U.S. Application Data

[63] Continuation of Ser. No. 706,329, Jul. 19, 1976, abandoned.

[30] Foreign Application Priority Data

Jul. 23, 1975 [JP] Japan .................................... 50-89207
Jul. 23, 1975 [JP] Japan .................................... 50-89209

[51] Int. Cl.$^3$ ............................................. C12N 11/14
[52] U.S. Cl. .................................... 435/176; 435/177; 435/178; 435/179; 435/182
[58] Field of Search .................... 195/63, 68, DIG. 11; 435/176, 182

[56] References Cited

U.S. PATENT DOCUMENTS

| 3,788,950 | 1/1974 | Hicks et al. ............. 195/DIG. 11 X |
| 3,838,007 | 9/1974 | Van Velzen ............ 195/DIG. 11 X |
| 3,859,169 | 1/1975 | O'Driscoll et al. ..................... 195/63 |
| 3,860,490 | 1/1975 | Guttag ................................. 195/108 |
| 3,933,587 | 1/1976 | Maeda et al. ......................... 195/68 |
| 3,962,038 | 6/1976 | Kawashima et al. ................. 195/68 |
| 4,025,391 | 5/1977 | Kawashima et al. ................. 195/68 |

FOREIGN PATENT DOCUMENTS 50-78640 2/1975 Japan .
51-26285 2/1976 Japan .

Primary Examiner—Lionel M. Shapiro
Attorney, Agent, or Firm—Ladas & Parry

[57] ABSTRACT

Enzymes are adsorbed on an adsorbent powder in an aqueous medium and a water-miscible monomer is added thereto, and said monomer is polymerized to form a porous gel lump through which a substrate solution can freely pass. The thus formed enzyme composition has long-lasting activity and thus the enzymes can be easily separated from the reaction system and can be used repeatedly.

9 Claims, No Drawings

METHOD FOR IMMOBILIZING ENZYMES

This is a continuation of application Ser. No. 706,329 filed July 19, 1976, now abandoned.

BACKGROUND OF THE INVENTION

This invention relates to the method for immobilization or fixation of enzymes or enzyme-containing microoganism cells by which enzymes are made insoluble in water and fixed on a vehicle or carrier.

It is well known that enzymes are used as the catalyst that effectively promotes many chemical reactions which cannot be carried out with ordinary chemical catalysts and are indispensable materials in the fields of food industry, pharmaceutical industry and other industries. Heretofore, in most enzymatic reactions, enzymes are used in an aqueous phase and they are discarded together with waste liquids after the reaction. In most cases, it is very difficult from both technical and economic viewpoints to recover enzymes from the reaction mixture for repeated use thereof. Therefore, enzymatic reactions are always carried out batch by batch. So, if a method to insolubilize enzymes and immobilize them in a form in which substrates can be continually contacted with them, enzymes can be used repeatedly and enzymatic reaction processes can be carried out continuously.

So far, it has been attempted to chemically combine enzymes with water-insoluble substances such as synthetic macromolecules so as to fix them. However, the activity of enzymes is very sensitive to change in the molecular structure thereof, and in most cases enzymes are remarkably deactivated by such chemical fixation. Therefore such methods are not successfully employed in practical application. Also it was proposed to make enzymes be adsorbed on an absorbent such as active carbon, active terra alba (white earth), etc. (U.S. Pat. No. 2,717,852, 1955). But in this method, the enzyme adsorbed thereon is easily desorbed as it is repeatedly used for reaction. This method is unpractical because of short life of the enzyme composition. Further, the so-called entrapping or inclusion method is known. For instance, a method which comprises polymerizing a water-soluble monomer suh as acrylamide in a solution containing an enzyme (K. Kawashima et al., Biotech. Bioeng. 16, 609, 1974) and a method which comprises cross-linking polyvinyl alcohol in its aqueous solution containing an enzyme (H. Maeda et al., Biotech, Bio-eng. 15 827, 1973) have been proposed. However, these polymers remarkably swell with water and therefore the inclusion mass is in the state of a gel lump that has no pores or voids, and therefore it is necessary to dry up the lump and pulverize it in order to convert it to a form in which the enzyme can contact with a substrate substance. This is a troublesome treatment and involves high possibility of desorption and/or deactivation of the enzyme during such treatment.

We have endeavored to find out a simple and effective method of immobilizing or fixing enzymes securing the long-lasting enzyme activity and now provide a new method of this invention.

SUMMARY OF THE INVENTION

The method of this invention comprises making an enzyme or enzyme-containing microorganism cells adsorbed on an adsorbent selected from the undermentioned Group A in an aqueous solution or dispersion of the enzyme, and thereafter mixing the thus obtained dispersion with a monomer selected from the undermentioned Group B, and polymerizing said monomer to form a porous gel composition containing immobilized enzyme or cells.

Group A—Adsorbents

Inorganic natural earth adsorbents, synthetic inorganic adsorbents, polypeptides, natural and synthesized amorphous carbon hydrate adsorbents. The powder size of the adsorbent should be 0.1 mm–5 mm, preferably 0.5 mm–3 mm.

Group B—Hydrophilic monomers

An acrylate or methacrylate ester or a mixture thereof represented by the general formula

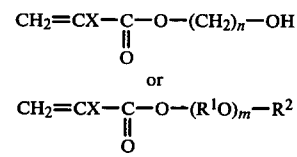

wherein $R^1$ is a group $-CH_2CH_2-$ or $-CH(CH_3)CH_2-$; $R^2$ is hydrogen, methyl or a group represented by

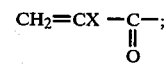

X is hydrogen or methyl; n is an integer 2, 3 or 4; and m is an integer 2–20, preferably 4–15, more preferably 4–12.

The monomer of Group B can be replaced by another polymerizable monomer or monomers (hereinafter called Group C monomers) in an amount not more than 30% of the total amount of the monomers.

The proportion of water and the polymerizable monomers (B and C) varies according to the properties desired for the formed gel such as porosity, density, distribution of voids, etc., and therefore is important factor that influences the effect of fixation of enzyme etc. Usually, on the basis of the weight of the total solution, a monomer or monomers are used in an amount of 80–0.5%, preferably 60–1%, more preferably 50–5%.

The amount of the adsorbent, that is, Group A materials, is up to the same weight of the used solution, although more then that can be used. The preferred amount is easily determined by trial and error.

The amount of enzyme to be fixed in the gel is not particularly limited. It depends upon adsorption capacity of the used adsorbent.

Polymerization can be carried out by means of radical initiators or light or ionizing radiations. Most enzymes are unstable against heat, therefore it is advantageous to carry out polymerization by means of light or an ionizing radiation at low temperatures. On the other hand, some enzymes are sensitive to radiation and are deactivated thereby. For such enzymes, polymerization is carried out by heating together with a free radical catalyst, preferably with a redox catalyst system at a temperature as low as possible. When light or radiations are employed, polymerization can be carried out at very low temperatures such as $-200°$ C., but preferred temperatures are between 0° C. and −80° C., more preferably −20° C.−−80° C.

The effect of this invention is that entrapped enzymes maintain high activity; enzymes are not easily released from the carrier; and immobilized enzymes have a long life.

DETAILED DESCRIPTION OF THE INVENTION

Specific examples of Group A adsorbent materials include: active terra alba (white earth), bentonite, kaolin, and other silicate materials; alumina, silica gel, molecular sieves, active carbon, ion exchange resins, starch, amylopectin, amylose, cellulose, cellulose nitrate, cellulose acetate, cellulose butyrate, cellulose phosphate, hydroxyethylcellulose, carboxymethylcellulose, cyanoethylcellulose, starch phosphate, starch nitrate, carboxymethyl starch, hydroxyethyl starch, agar, gelatin, collagen, etc.

Specific examples of Group B monomers include: hydroxyethyl methacrylate, hydroxyethyl acrylate, hydroxypropyl methacrylate, hydroxypropyl acrylate, hydroxybutyl methacrylate, hydroxybutyl acrylate, diethyleneglycol monomethacrylate, diethyleneglycol monoacrylate, triethyleneglycol monomethacrylate, triethyleneglycol monoacrylate, tetraethyleneglycol monomethacrylate, tetraethyleneglycol monoacrylate, polyethyleneglycol monomethacrylate, polyethyleneglycol monoacrylate, methoxydiethyleneglycol methacrylate, methoxydiethyleneglycol acrylate, methoxy triethyleneglycol methacrylate, methoxytriethyleneglycol acrylate, methoxytetraethyleneglycol methacrylate, methoxytetraethyleneglycol acrylate,, diethyleneglycol dimethacrylate, diethyleneglycol diacrylate, triethyleneglycol dimethacrylate, triethyleneglycol diacrylate, tetraethyleneglycol dimethacrylate, tetraethyleneglycol diacrylate, polyethyleneglycol dimethacrylate, polymethyleneglycol diacrylate, etc.

Specific example of Group C monomers include: styrene, divinylbenzene, vinyltoluene, alpha-methylstyrene, vinylalkylether, vinylpyridine, vinylpyrrolidone, vinylcarbazole, acrylic acid, methacrylic acid, acrylamide, methacrylamide, acrylonitrile, methacrylonitrile, methylolacrylamide, diacetonacrylamide, t-butylacrylamide, methylene-bis-acrylamide, methyl acrylate, methyl methacrylate, ethyl acrylate, ethyl methacrylate, n-propyl acrylate, n-propyl methacrylate, isopropyl acrylate, isopropyl methacrylate, butyl acrylate, butyl methacrylate, isobutyl acrylate, isobutyl methacrylate, octyl acrylate, octyl methacrylate, cyclohexyl acrylate, cyclohexyl methacrylate, lauryl acrylate, lauryl methacrylate, stearyl acrylate, stearyl methacrylate, glycidyl acrylate, glycidyl methacrylate, phenyl acrylate, phenyl methacrylate, benzyl acrylate, benzyl methacrylate, diethylaminoethyl acrylate, diethylaminoethyl methacrylate, vinyl acetate, vinyl propionate, itaconic acid, itaconic anhydride, maleic anhydride, triallyl cyanurate, diallyl itaconate, diallyl succinate, diallyl maleate, dipropargyl maleate, trimethylolethane triacrylate, trimethylolethane trimethacrylate, trimethylolpropane triacrylate, trimethylolpropane trimethacrylate, trimethylolbutane triacrylate, trimethylolbutane trimethacrylate, glycerol monoacrylate, glycerol monomethacrylate, ethylene diacrylate, ethylene dimethacrylate, neopentylglycol diacrylate, aeopentylglycol dimethacrylate, pentanediol monoacrylate and diacrylate, pentanediol monomethacrylate and dimethacrylate, hexanediol monoacrylate and diacrylate, hexanediol monomethacrylate and dimethacrylate, heptanediol monoacrylate and diacrylate, heptanediol monoacrylate and diacrylate, heptanediol monomethacrylate and dimethacrylate, etc.

Specific examples of enzymes to which the method of this invention is most successfully applicable include: alpha-amylase, beta-amylase, glucoamylase, cellulase, hemicellulase, beta-glucosidase, invertase, urease, alcohol dehydrogenation enzyme, lactic acid dehydrogenation enzyme, glucose-oxidase, hexokinase, D-aminoacid-oxidase arginase, papain, ficin, rennin, trypsin, glucose-isomerase, L-glutaric acid decarboxylase, alkaline protease, acidic protease, etc.

According to this invention, compositions containing immobilized enzymes, which permit free passing of substrate solutions, during which enzymatic reaction occurs, is obtained. The compositions are successfully obtained by combined use of a Group A absorbent and a Group B polymerizable monomer. If a Group A absorbent is used in combination with a water-soluble monomer other than Group B such acrylamide, the produced polymer absorbs water and forms a swollen hydrogel which includes the adsorbent on which an enzyme is adsorbed leaving no pores or voids. Therefore, the included enzyme cannot be contacted with a substrate substance, unless it is dried up and pulverized. During such treatments, the enzyme will be deactivated or released from the carrier.

In contrast, when a Group B monomer is used, it is miscible with water and the adsorbent containing an enzyme is well dispersed therein. But, when subjected to polymerization treatment, the monomer forms a porous polymer composition deposited from the aqueous phase including the absorbent on which the enzyme is adsorbed.

In the prior art processes, when an enzyme is entrapped in a polymer, there occur considerable release and/or deactivation of the enzyme. In the process of this invention, as the enzyme is adsorbed stable on an adsorbent, and the adsorbent is entrapped by a polymer, and therefore there is no chance for the enzyme of release and deactivation thereof. If the enzyme is simply adsorbed on an adsorbent or simply entrapped in a polymer, the enzyme will be released from the carrier thereof as it is repeatedly used. In our invention, an enzyme is adsorbed on an adsorbent and further included in a three-dimensional reticular structure of polymer, and therefore the enzyme composition is provided with good durability.

The immobilized enzyme composition obtained in accordance with this invention is of a porous structure, and therefore the enzyme is in the condition under which it is readily contacted with a substrate substance which passes through the three-dimensional structure of the polymer without any after treatment required.

This invention is based on our finding a combination of an adsorbent and specific polymerizable monomer, which is not inferable from the known prior art disclosure.

In accordance with this invention, place a dispersion comprising a Group A absorbent, on which an enzyme is adsorbed, a Group B monomer and water in, say, a column which is provided with a cook at the bottom thereof, and polymerize the monomer therein; then a polymer of the porous gel state is formed deposited from water, and an enzymatic reaction can be continuously carried out by pouring a substrate solution into the top of the column with the bottom cock open. If a part of the Group B monomer is replaced with a polyfunctional monomer (selected from Group C), cross-linking occurs or is strengthened and a three-dimensional reticular structure will well develop in the formed polymer, and enzymes are better entrapped allowing passing of the substrate solution.

That is, by selective addition of a Group C monomer, porosity of the formed polymer can be widely varied, although the prosity is regulated by the proportion of water and the Group B monomer only. Because many of the Group C monomers are poorly water-miscible or water-insoluble and addition thereof modifies affinity and the formed polymer with water. Therefore the amount of the Group C monomer to be used is limited as mentioned above. If a too large amount thereof is used, the formed polymer will become macroscopically heterogeneous, and the object of this invention will not be achieved.

When enzyme-producing microorganisms themselves are used instead of enzymes, some of them can be used as they are, but some of them are used after their cells are disintegrated by means of ultrasonic wave, etc.

Now the invention is specifically explained by way of working examples.

EXAMPLE 1

A 250 μg portion of alpha-amylase was dissolved in 0.8 ml of the phosphoric acid buffer solution (pH 6.9). The thus obtained enzyme solution was put into a glass ampoule the outside diameter of which is 1 cm and 0.4 g of pulverized silica gel was added thereto. After the enzyme was adsorbed on the silica gel, 0.2 ml of 2-hydroxyethyl methacrylate was added, and thereafter the ampoule was sealed in the air. The contents of the ampoule was irradiated with gamma-rays from Co 60 at $-24°$ C. at the dose rate of $1\times 10^6$ R/hr for one hour. A porous polymer gel lump was obtained with the polymerization yield of 97.8%.

This gel was divided into small pieces and used for the following enzymatic reaction without purification, drying or pulverization, etc. That is, the gel pieces were added to 5 ml of a 2% soluble starch solution allowing reaction for one hour at 40° C. The remaining enzymatic activity was colorimetrically determined by the 3,5-dinitrosalicylic acid method.

The remaining activity of the enzyme is represented by the proportion (%) of the activity of the immobilized and used enzyme to that of the enzyme in the free state. The results after the repetition of the reaction are shown in Table 1.

Table 1

| Method of immobilizing enzyme | Ratio (%) of remaining activity to that prior to immobilization | | | | | |
|---|---|---|---|---|---|---|
| | After 1 run | After 10 runs | After 100 runs | After 200 runs | After 400 runs | After 600 runs |
| Method of Example 1 | 85.4 | 85.1 | 84.3 | 83.6 | 82.4 | 81.1 |
| Known entrapping method* | 59.6 | 33.4 | 27.2 | 24.3 | 20.2 | 18.4 |
| Adsorption method** | 96.3 | 3.2 | — | — | — | — |

*Immobilizing enzyme by polymerizing the same amount of 2-hydroxyethyl methacrylate added to the enzyme solution
**Immobilizing enzyme by simple adsorption on the same amount of pulverized silica gel added to the enzyme solution
— Undeterminable

EXAMPLE 2

Instead of 2-hydroxyethyl methacrylate (0.2 ml) in Example 1, 0.14 ml of 2-hydroxyethyl methacrylate and 0.06 g of methylolacrylamide were used and the same enzyme was immobilized in the same way as in Example 1, and the remaining enzymatic activity was determined in the same way. The results are as follows.

Table 2

| No. of reaction runs | 1 | 10 | 100 |
|---|---|---|---|
| Remaining activity (%) | 88.5 | 87.9 | 88.1 |

In comparison with the case where only 2-hydroxyethyl methacrylate was used, the remaining activity was somewhat raised. It is understood that, by addition of methylolacrylamide, solubility of monomers was modified and the formed polymer was deposited from water in the more minutely dispersed condition, and thus the enzyme was more easily contacted with the substrate.

EXAMPLE 3

Instead of 2-hydroxyethyl methacrylate (0.2 ml) in Example 1, 0.14 ml of 2-hydroxyethyl methacrylate and 0.06 ml of diallyl itaconate were used and the same enzyme was immobilized in the same way as in Example 1, and the remaining activity was determined in the same way. The results are shown in Table 3.

Table 3

| No. of reaction runs | 1 | 10 | 100 |
|---|---|---|---|
| Remaining activity (%) | 89.1 | 89.2 | 88.9 |

In comparison with the case where only 2-hydroxyethyl methacrylate was used, the remaining activity was somewhat raised. It is understood that, by addition of diallyl itaconate, a denser reticular structure was formed and thus the enzyme was better trapped therein.

EXAMPLE 4

A 600 μg portion of glucoamylase was dissolved in 0.9 ml of the acetic acid buffer solution (pH 4.5), the thus obtained enzyme solution was put into a glass ampoule the outside diameter of which is 1 cm, and 0.2 g of kaolin was added thereto. After the enzyme was adsorbed on the kaolin, 0.1 ml of triethyleneglycol monomethacrylate was added, and thereafter the ampoule was sealed in a nitrogen atmosphere. The contents of the ampoule was irradiated with gamma-rays from Co 60 at $-52°$ C. at the dose rate of $1\times 10^5$ R/hr for 2 hours. A porous polymer gel was obtained with the polymerization yield of 87.1%.

This gel was, without purification, drying and pulverization, divided into minute pieces and added to 5 ml of a 2% maltose solution in the acetic acid buffer solution (pH 4.5). The solution was allowed to stand for reaction at 40° C. for 30 minutes. Activity of the enzyme was determined as the amount of glucose with the glucose determination reagent (supplied by Nagase Sangyo K. K.) and the remaining activity was calculated therefrom. The results of repetition of the reaction are shown in Table 4.

Table 4

| Method of immobilizing enzyme | Ratio (%) of remaining activity to that prior to immobilization | | | | | |
|---|---|---|---|---|---|---|
| | After 1 run | After 10 runs | After 100 runs | After 300 runs | After 500 runs | After 700 runs |
| Method of Example 4 | 79.1 | 78.8 | 78.0 | 77.1 | 76.4 | 75.0 |
| Simple entrapping method* | 61.4 | 34.9 | 29.8 | 24.1 | 20.2 | 16.4 |
| Adsorption method** | 98.2 | 1.4 | — | — | — | — |

*Immobilizing enzyme by polymerizing the same amount of tri-ethyleneglycol monomethacrylate added to the enzyme solution.
**Immobilzing enzyme by simple adsorption on the same amount of kaolin
— Undeterminable

EXAMPLE 5

A 100 mg portion of a glucose-isomerase producing ray fungus (*Streptomyces phaeochromogenensis*) was collected from a colony thereof and was dispersed without disintegration in 4.5 ml of the phosphoric acid buffer solution (pH 6.9), and 1.0 g of pulverized active carbon was added thereto. After the dispersion was well contacted with the active carbon, 0.5 ml of 2-hydroxyethyl methacrylate containing 5% ethyleneglycol dimethacrylate was added. The mixture was placed in an ampoule and the ampoule was sealed. It was irradiated with gamma-rays from Co 60 at $-78°$ C. at the dose rate of $1 \times 10^6$ R/hr for one hour, and a polymer gel lump containing the immobilized enzyme was obtained with the polymerization yield of 92.9%.

The gel lump was divided into minute pieces and contacted with an aqueous solution containing 2% glucose as the substrate at 40° C. for one hour for reaction. The enzymatic activity was determined as the amount of fractose by the cysteine-carbazole method and the percentage of the remaining activity was calculated. The results of repetition of the reaction was shown in Table 5.

Table 5

| Method of immobilizing enzyme | Ratio (%) of remaining activity to that prior to immobilization | | | | | |
|---|---|---|---|---|---|---|
| | After 1 run | After 10 runs | After 100 runs | After 300 runs | After 500 runs | After 700 runs |
| Method of Example 5 | 76.4 | 76.3 | 75.7 | 75.1 | 74.2 | 73.6 |
| Simple entrapping method* | 71.4 | 58.4 | 46.9 | 37.1 | 27.0 | 18.4 |
| Adsorption method** | 98.2 | 2.1 | — | — | — | — |

*Immobilizing enzyme by polymerizing the same amount of the abovementioned monomer mixture added to the enzyme solution
**Immobilzing enzyme by simple adsorption on the same amount of pulverized active carbon
— Undeterminable

EXAMPLE 6

A 2500 μg portion of alpha-amylase was dissolved in 8 ml of the phosphoric acid buffer solution (pH 6.9), and 4 g of gelatin powder and 2 ml of 2-hydroxyethyl methacrylate were added thereto and were well mixed. The mixture was placed in a long cylindrical glass ampoule the inside diameter of which is 10 cm and both ends of the ampoule were sealed in the air. The contents of the ampoule was irradiated with gamma-rays from Co 60 at $-78°$ C. at the dose rate of $1 \times 10^6$ R/hr for one hour. A porous polymer gel was obtained with the polymerization yield of 95.8%.

Both ends of the ampoule were cut off and a 2% aqueous solution of soluble starch was continuously poured into the top of the column at the flow rate of 5 ml/hr at 40° C. The operation was continued up to 30 days.

The remaining enzymatic activity of the immobilized enzyme in the column was determined colorimetrically by the 3,5-dinitrosalicylic acid method.

The remaining activity is represented by the ratio (%) of the activity of the immobilized enzyme to that of the enzyme in the free state. The results are shown in Table 6.

Table 6

| Method of immobilizing enzyme | Ratio (%) of remaining activity to that prior to immobilization | | | |
|---|---|---|---|---|
| | After 1 day | After 10 days | After 20 days | After 30 days |
| Method of Example 6 | 87.4 | 87.4 | 87.3 | 87.1 |
| Simple entrapping method* | 32.3 | 24.5 | 20.1 | 18.4 |
| Adsorption method** | 2.0 | — | — | — |

*Immobilizing enzyme by polymerizing the same amount of 2-hydroxyethyl methacrylate added to the enzyme solution
**Immobilizing enzyme by mixing with the same amount of gelatin powder
— Undeterminable

EXAMPLE 7

Instead of 2-hydroxyethyl methacrylate (2 ml) in Example 6, mixtures of 2-hydroxyethyl methacrylate and hexanediol diacrylate of various proportions were used and the same enzyme was immobilized in the same way as in Example 6, and the remaining activity was determined in the same way. The results are shown in Table 7.

Table 7

| Amount of 2-hydroxyethyl methacrylate (ml) | 1.9 | 1.8 | 1.7 | 1.6 | 1.4 | 1.2 |
|---|---|---|---|---|---|---|
| Amount of hexanediol diacrylate (ml) | 0.1 | 0.2 | 0.3 | 0.4 | 0.6 | 0.8 |
| Remaining activity after 30 day's continuous reaction (%) | 89.9 | 89.8 | 90.6 | 89.9 | 88.5 | 78.2 |

It is understood that by the addition of hexanediol diacrylate, water-affinity and cross-linking density of the polymer were modified and a structure in which substrate substance is more easily diffuses was formed.

EXAMPLE 8

Instead of 2-hydroxyethyl methacrylate (2 ml) in Example 6, a mixture of 1.5 ml of 2-hydroxyethyl methacrylate and 0.3 ml of vinylpyrrolidone and 0.2 ml of ethylene dimethacrylate was used and the same enzyme was immobilized in the same way as in Example 6. The remaining activity of the enzyme after 30 days' continuous reaction was 90.2%.

EXAMPLE 9

A 6000 μg portion of glucoamylase was dissolved in 7 ml of the acetic acid buffer solution (pH 4.5), and 6.0 g of starch and 3 ml of triethyleneglycol monomethacrylate were added thereto, and mixed well. The mixture was placed in a long cylindrical glass ampoule the inside diameter of which is 20 mm and the ampoule was sealed in the nitrogen atmosphere. The contents of the ampoule was irradiated with gamma-rays from Co 60 at $-24°$ C. at the dose rate of $5 \times 10^5$ R./hr for 2 hours, and a column of a polymer gel containing the immobilized enzyme was obtained by cutting off both ends of the ampoule. The polymerization yield was 91.3%.

The enzymatic reaction was carried out by continuously letting a 2% maltose solution pass through the column of the polymer gel at the flow rate of 4 ml/hr at 40° C. The remaining activity of the enzyme in the column was colorimetrically determined by the glucose determination reagent (supplied by Nagase Sangyo K. K.). The results are shown in Table 8.

Table 8

| Method of immobilizing enzyme | Ratio (%) of remaining activity to that prior to immobilization | | | |
|---|---|---|---|---|
| | After 1 day | AFter 10 days | After 20 days | After 30 days |
| Method of Example 9 | 84.4 | 84.4 | 84.3 | 84.1 |
| Simple entrapping method* | 40.2 | 30.2 | 24.4 | 18.1 |
| Adsorption method** | 10.2 | 2.1 | — | — |

*Immobilizing enzyme by polymerizing the same amount of tri-ethyleneglycol monomethacrylate added to the enzyme solution
**Immobilizing enzyme by mixing with the same amount of starch
— Undeterminable

EXAMPLE 10

A one gram portion of cellulose was dissolved in 8 ml of the acetic acid buffer solution (pH 4.5), and 5 g of carboxymethylcellulose powder and 2 ml of 2-hydroxyethyl methacrylate containing 5% trimethylolpropane trimethacrylate were added thereto and mixed well. The mixture was placed in a long cylindrical glass ampoule the inside diameter of which is 10 mm, and the ampoule was sealed in the air.

The contents of the ampoule was irradiated with gamma-rays from Co 60 at $-48°$ C. at the dose rate of $1 \times 10^6$ R./hr for 2 hours. Thus a column of a polymer gel containing immobilized enzyme was obtained after both ends of the ampoule were cut off. The polymerization yield was 96.4%.

The enzymatic reaction was continuously carried out by passing a 2% cellulose solution through the column at the flow rate of 6 ml/hr at 40° C. The remaining activity of the enzyme in the column was colorimetrically determined by the phenol method. The results are shown in Table 9.

Table 9

| Method of immobilizing enzyme | Ratio (%) of remaining activity to that prior to immobilization | | | |
|---|---|---|---|---|
| | After 1 day | After 10 days | After 20 days | After 30 days |
| Method of Example 10 | 72.4 | 72.1 | 71.3 | 70.9 |
| Simple entrapping method* | 31.4 | 26.4 | 20.2 | 17.1 |
| Adsorption method** | 3.4 | 1.1 | — | — |

*Immobilizing enzyme by polymerizing the same amount of tri-methylolpropane methacrylate added to the enzyme solution.
**Immobilizng enzyme by mixing with the same amount of carboxymethylcellulose.
— Undeterminable

What we claim is:

1. A method for immobilizing enzymes or enzyme-containing cells comprising (a) adsorbing said enzymes or enzyme-containing cells on an adsorbent selected from the group consisting of inorganic natural earth adsorbents, synthetic inorganic adsorbents and active carbon in an aqueous medium, (b) admixing the aqueous dispersion of said adsorbent on which enzymes or enzyme-containing cells have been adsorbed with a polymerizable monomer selected from the groups consisting of compounds represented by the general formula $$CH_2=CX-\underset{\underset{O}{\|}}{C}-O-(CH_2)_n-OH \text{ or}$$

$$CH_2=CX-\underset{\underset{O}{\|}}{C}-O-(R^1O)_m-R^2,$$

wherein $R^1$ is a group $-CH_2CH_2-$ or $-CH(CH_3)CH_2-$, $R^2$ is hydrogen or methyl or a group represented by $$CH_2=CX-\underset{\underset{O}{\|}}{C}-,$$

X is hydrogen or methyl, n is an integer 2, 3 or 4 and m is an integer from 2 to 20 and (c) effecting polymerization at a temperature between $-20°$ C. and $-80°$ C., to form a porous gel lump in which enzymes or enzyme-containing cells are distributed adsorbed on inorganic adsorbent, and through which a substrate solution can freely pass.

2. The method as defined in claim 1, wherein said adsorbent is selected from the group consisting of active terra alba, bentonite, kaolin, alumina, silica gel, molecular sieves and active carbon, and said monomer B is selected from the compound represented by the general formula:

$$CH_2=CX-\underset{\underset{O}{\|}}{C}-O-(CH_2)_n-OH$$
or
$$CH_2=CX-\underset{\underset{O}{\|}}{C}-O-(R^1O)_m-R^2$$

wherein $R_1$ is $-CH_2CH_2-$, $R^2$ is hydrogen, X is hydrogen or methyl, n is 2, 3 or 4, and m is 2, 3 or 4.

3. The method as defined in claim 2, wherein said adsorbent is selected from the group consisting of silica gel, kaolin and active carbon.

4. The method as defined in claim 3, wherein said B monomer is selected from the group consisting of 2-hydroxyethyl methacrylate and triethyleneglycol monomethacrylate.

5. The as defined in claim 1, wherein said B monomer contains a second monomer C having water-miscibility different from that of said Group B monomer in amount up to 30% of the total weight of the monomers.

6. The method as defined in claim 5, wherein said adsorbent is selected from the group consisting of active terra alba, bentonite, kaolin, alumina, silica gel, molecular sieves, and active carbon and said water-miscible monomer is selected from the compounds represented by the general formula:

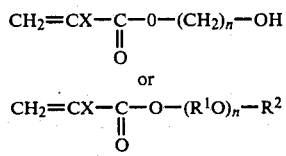

wherein $R^1$ is $-CH_2CH_2-$, $R^2$ is hydrogen, X is hydrogen or methyl, n is 2, 3 or 4, and m is 2, 3 or 4, and said second monomer is a polyfunctional partly water-miscible monomer.

7. The method as defined in claim 6, wherein said adsorbent is selected from the group consisting of silica gel, kaolin, and active carbon.

8. The method as defined in claim 7, wherein said monomer B is selected from the group consisting of 2-hydroxyethyl methacrylate and triethyleneglycol monomethacrylate, and the second monomer is selected from the group consisting of methylolacrylamide, diallyl itaconate, ethyleneglycol dimethacrylate, hexanediol diacrylate, vinylpyrrolidone, trimethylolpropane trimethacrylate.

9. A porous three dimensional reticular structure comprising adsorbed enzyme or enzyme-containing cells whenever obtained by (a) adsorbing said enzymes or enzyme-containing cells on an adsorbent selected from the group consisting of inorganic natural earth adsorbents, synthetic inorganic adsorbents and active carbon in an aqueous medium, (b) admixing the aqueous dispersion of said adsorbent on which enzymes or enzyme-containing cells have been adsorbed with a polymerizable monomer selected from the groups consisting of compounds represented by the general formula

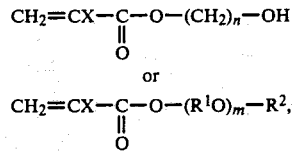

wherein $R^1$ is a group $-CH_2CH_2-$ or $-CH(CH_3)CH_2-$, $R^2$ is hydrogen or methyl or a group represented by

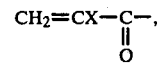

X is hydrogen or methyl, n is an integer 2, 3 or 4 and m is an integer from 2 to 20 and (c) effecting polymerization at a temperature between $-20°$ C. and $-80°$ C., to form a porous gel lump in which enzymes or enzyme-containing cells are distributed adsorbed on inorganic adsorbent, and through which a substrate solution can freely pass.

* * * * *